United States Patent [19]

Rosner et al.

[11] Patent Number: 4,774,321

[45] Date of Patent: Sep. 27, 1988

[54] DP100 EGF AND INSULIN-BINDING PROTEIN FROM DROSOPHILA CELLS

[75] Inventors: Marsha R. Rosner, Lexington; Karol L. Thompson, Cambridge; J. Victor Garcia, Cambridge; M. Patrizia Stoppelli, Cambridge, all of Mass.

[73] Assignee: Massachusetts Institute of Technology, Cambridge, Mass.

[21] Appl. No.: 936,325

[22] Filed: Dec. 1, 1986

[51] Int. Cl.$^4$ ........................ C08L 89/00; C12P 21/00
[52] U.S. Cl. .................................... 530/350; 530/399; 530/391; 530/413; 436/501
[58] Field of Search ............... 530/350, 399, 413, 303, 530/305; 436/817, 501, 503; 424/101

[56] References Cited

U.S. PATENT DOCUMENTS 4,634,665 1/1987 Axel et al. ........................... 935/34

OTHER PUBLICATIONS

Thompson et al, Proc. Natl. Acad. Sci. USA, 82, 8443, Dec. (1985).
Livneh et al, *Cell*, 40(3), 599–607, (1985).
Lev et al, Dev. Biol., 110, 499–502, (1985).
Becker et al, Biotech Advs, 1, 247–261, (1983).

*Primary Examiner*—Howard E. Schain
*Assistant Examiner*—Jeff P. Kushan

*Attorney, Agent, or Firm*—Patrea L. Pabst

[57] ABSTRACT

A novel 100 kDa protein from *Drosophila melanogaster* (dp100) that recognizes both mammalian epidermal growth factor (EGF), insulin and insulin-related growth factors, and crossreacts with antisera against the human EGF receptor. The binding spectrum and relative binding affinities of dp100 for growth factors and hormones, related and unrelated to EGF or insulin, demonstrate that dp100 binds to insulin-like and EGF-like factors with dissociation constants ranging from $10^{-6}$M to $10^{-9}$M. Dp100 binds to human synthetic transforming growth factor-alpha (TGF-alpha) and insulin-like growth factor-II with the highest affinity and, unlike the mammalian EGF receptor, has the unique ability to differentiate between EGF and TGF-alpha with a difference in affinity of three orders of magnitude. Further, dp100 is able to differentiate on the basis of binding affinity between native TGF-alpha, TGF-alpha that has been synthesized chemically and TGF-alpha that has been produced in *E. coli* using recombinant DNA technology. The specific competition of the EGF-like and insulin-like growth factors for dp100 provides a means for identifying or assaying for the presence of, and structural and functional modifications of, these growth factors and hormones, as well as a means for purification or removal of these substances.

6 Claims, 2 Drawing Sheets

□ TGF-ALPHA produced by recombinant technology
○ TGF-ALPHA
△ TGF-ALPHA produced by chemical synthesis

DP100 EGF AND INSULIN-BINDING PROTEIN FROM DROSOPHILA CELLS

BACKGROUND OF THE INVENTION

The U.S. Government has certain rights in this invention by virtue of National Cancer Institute CA35541 and National Institute of Health Toxicology Training Grant T32-E507020.

The present invention is in the area of biological compounds and, in particular, a method and protein which specifically binds growth factors and hormones.

The tyrosine-specific protein kinases have been implicated in the regulation of cell proliferation in vertebrate species. This kinase family includes the retroviral transforming proteins related to pp60$^{src}$ and the receptors that bind epidermal growth factor (EGF), insulin, platelet-derived growth factor, and insulin-like growth factor I. The kinase active site is strongly conserved between members of this family in terms of amino acid sequence, substrate utilization, and antigenic crossreactivity. For example, the receptors for EGF and insulin can be immunoprecipitated by antibodies to pp60$^{src}$ and can utilize common substrates for tyrosine phosphorylation, including a synthetic peptide corresponding to the autophosphorylation site of pp60$^{src}$. The relationship between growth factor receptors and the src-related oncogenes is further extended by evidence that the EGF receptor gene appears to be the normal cellular counterpart of v-erbB, the avian erythroblastosis virus oncogene.

Conservation of members of the tyrosine kinase family has been demonstrated to extend to Drosophila. Gene sequences related to the retroviral oncogenes src, abl, and erbB have been cloned from the Drosophila genome. Sequence comparison of the Drosophila c-erbB with human EGF receptor cDNAs indicates that there is significant homology in the kinase region and in part of the extracellular domain. In the 170-kDa mammalian EGF receptor, the EGF binding domain is situated on the cysteine-rich, extracellular portion, while the cytoplasmic side contains the tyrosine kinase region and sites that serve as substrates for autophosphorylation and for phosphorylation by protein kinase C.

The insulin receptor also appears to be evolutionarily conserved. Isolated from Drosophila by affinity chromatography, the receptor is reportedly structurally similar to its mammalian counterpart, which exists as a disulfide-bonded heterodimer of alpha and beta subunits. In both mammalian and Drosophila insulin receptors, the insulin binding site is located on the 125- to 135-kDa alpha subunit, whereas the 90-kDa beta subunit contains the tyrosine kinase region.

Identification and characterization of homologs of mammalian growth regulatory proteins in lower organisms is an approach that can potentially yield new and relevant insights into the mechanism of action of these proteins. In vertebrates, growth factors that are members of the insulin and epidermal growth factor (EGF) families are integrally involved in the stimulation of mitogenesis and control of cellular metabolism. Further understanding of their biochemical interactions could benefit from identification and examination of proteins that bind these factors in genetically characterized lower organisms.

It is therefore an object of the present invention to provide a method and means for identifying and characterizing growth factors and hormones including epidermal growth factor (EGF), insulin, platelet-derived growth factor and insulin-like growth factor I.

It is a further object of the present invention to provide Drosophila proteins which can be used in such a method for identifying and characterizing growth factors and hormones.

It is a still further object of the present invention to provide such a Drosophila protein that can bind to a number of hormones and growth factors with a binding affinity unique to each hormone or growth factor or its source for use in purification of and assays for characterizing growth factors and hormones and the cells which produce the substances.

SUMMARY OF THE INVENTION

A 100 kDa protein isolated from the membranes and cytoplasm of Drosophila cells which selectively binds epidermal growth factor and insulin, and proteins related thereto, and is recognized by antisera against the epidermal growth factor receptor.

The protein is characterized by its ability to bind this specific family of proteins. It is particularly useful in assays for normal and abnormal proteins and cells which produce these proteins since the dp100 protein binds to each protein with a distinct binding affinity, having dissociation constants ranging from $10^{-6}$ to $10^{-9}$ M for insulin-like and epidermal growth factor-like growth factors. For example, the 100 kDa protein has the unique ability to differentiate between EGF and human synthetic transforming growth factor-alpha (TGF-alpha) with a difference in affinity of three orders of magnitude. Since some cells are characterized by the production of proteins such as EGF and TGF-alpha in excessively high levels following transformation, the binding of the protein can also be used as a qualitative assay for a change in the state of the cells producing the proteins bound by the 100 kDa protein. The dp100 protein is also useful in processes for the purification or removal of those substances bound by the dp100 protein.

DETAILED DESCRIPTION OF THE INVENTION

Figure 1A:
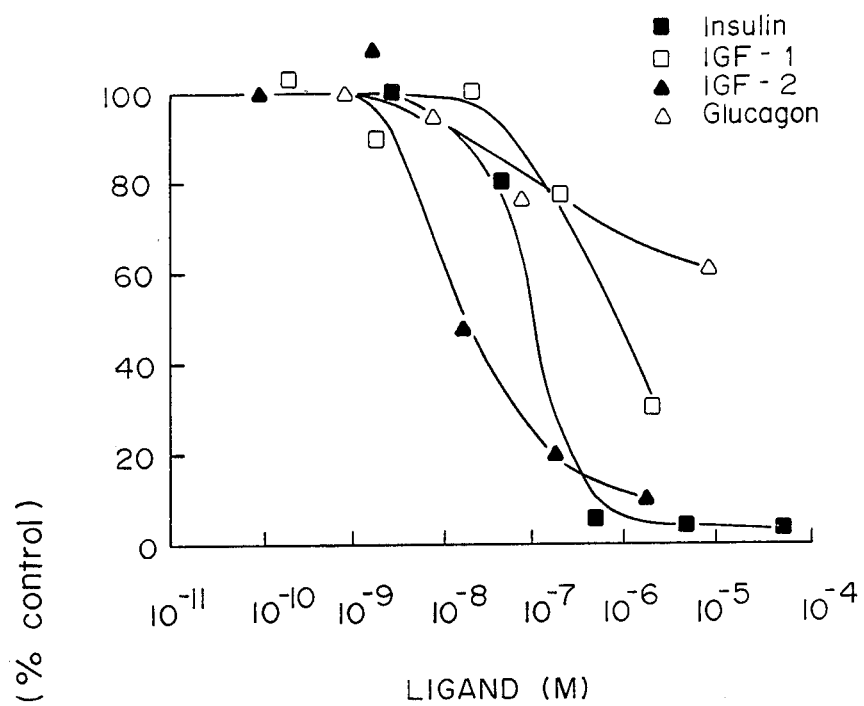
FIG. 1 are graphs of the competitive binding of labelled insulin to dp100 in the presence of insulin-like and EGF-like growth factors: insulin, IGF-1, IGF-2, Glucagon (a) and TFG-alpha, EGF, NGF (b), using Drosophila membrane immunoprecipitates crosslinked with labelled insulin in the presence of unlabelled growth factors, preparation and scanning of autoradiograms, and quantitation of the relative amount of labelled dp100. Insulin binding is expressed as percent of controls containing no competitor ligand (100%).
Figure 1B:
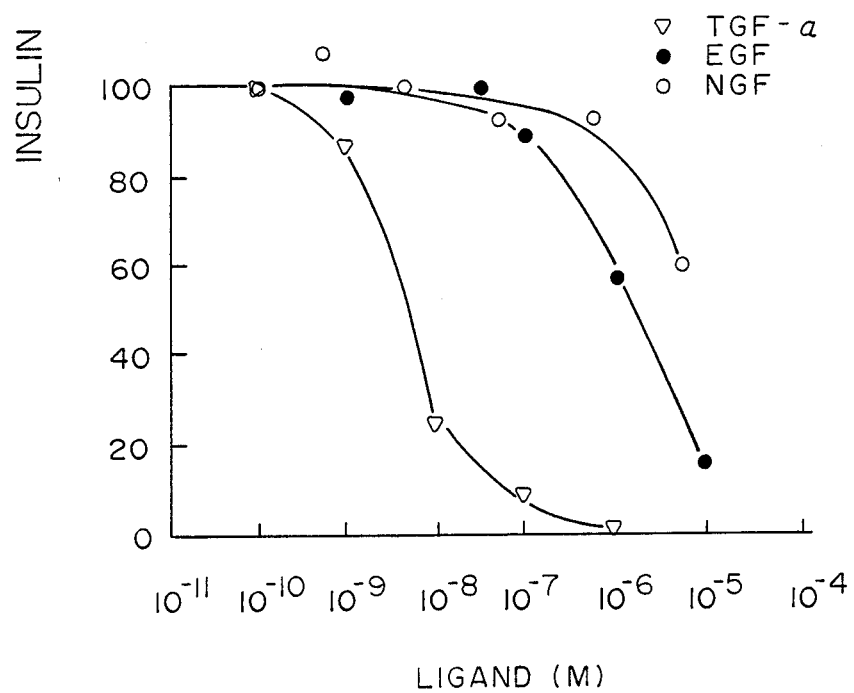

A unique growth factor binding protein for both insulin and EGF, designated dp100, has been identified and isolated by screening Drosophila cell lines for proteins related to the EGF receptor using polyclonal antisera that recognizes EGF receptors from a variety of species, including human, rodent and the avian V-erb product. This antisera reacts primarily with cytoplasmic determinants of the EGF receptor and can immunoprecipitate the product of the oncogene, p185, which is homologous to the EGF receptor in the kinase region.

The dp100 protein selectively recognizes other EGF-like and insulin-like growth factors, as shown by the interaction of dp100 with growth factors related and unrelated to both families. Not only does the dp100 protein specifically bind to all of the insulin and EGF-related growth factors tested; these insulin- and EGF-like factors compete for binding to dp100. Dp100 is very selective in spite of its broad specificity range, and, unlike the human EGF receptor, is able to discriminate between EGF and synthetic TGF-alpha. Thus, EGF-like and insulin-like growth factors can compete for binding with high specificity to a single protein.

The dp100 is isolated and the binding affinity determined as follows.

Materials and Methods

Cells: Drosophila Schneider L2 cells, a gift from M. Pardue, Massachusetts Institute of Technology, Biology Department, Cambridge, MA, are grown in M3 medium with 10% fetal calf serum. Drosophila $K_c$ cells, obtained from the Massachusetts Institute of Technology Cell Culture Center, ar grown in D22 medium. The Drosophila cell lines are maintained at 23° C. Mammalian cell lines are grown in Dulbecco's modified Eagle's medium supplemented with serum (10% fetal calf serum for the human epidermold carcinoma cell line A431 and 10% calf serum for the mouse fibroblast line Swiss 3T3). A431 cells are obtained from the American Type Culture Collection, Rockville, MD. Swiss 3T3 cells are provided by H. Green of the Harvard Medical School, Boston, MA.

Antisera: polyclonal rabbit anti-EGF receptor antiserum is prepared against denatured EGF-R from A431 cells as described by S. Decker, Arch. Biochem. Biophys. 229, 621-626 (1984). Antiserum prepared against affinity-purified rat insulin receptor is provided by S. Jacobs Burroughs Wellcome Research,. Triangle Park, NC. Growth factors are obtained from the following sources: murine EGF (receptor grade and HPLC purified) and porcine insulin from Biomedical Technologies Inc., Norwood, MA, $^{125}$I-TGF-alpha and $^{125}$I-TGF-beta from H. Massague of the University of Massachusetts, Worcester, MA, TGF-alpha made by recombinant techniques (Genentech, Inc., San Franciso, CA), IGF-I (Amgen, Thousand Oaks, CA), IGF-II (M. Czech, University of Massachusetts, Worcester, MA, synthetic human TGF-alpha (J. Tam, Rockefeller University, NY), recombinant human TGF-alpha (R. Derynck, Genentech, Inc., San Francisco, CA), NGF (G. Johnson, University of Massachusetts, Worcester, MA), $^{125}$I-PDGF (J. Votano and H. Antoniades, Harvard Medical School, Boston, MA), PTH and glucagon (Sigma Chemical Co., St. Louis, MO), human urokinase amino terminal fragment (F. Blasi, Napoli, Italy). $^{125}$I-EGF is prepared by the chloramine T method, while insulin and TGF-alpha are iodinated using Enzymobeads (BioRad Laboratories, Richmond, CA). The specific activities are approximately 50-150 microCi/microgram.

Membrane Preparation: A431 cells are dislodged from tissue culture plates by incubation in phosphate-buffered saline (137 mM NaCl, 2.,7 mM KCl, 8.1 mM Na$_2$HPO$_4$, 1.5 mM KH$_2$PO$_4$ pH 7.4) (PBS) containing 0.5 mM EDTA at 37° C. Swiss 3T3 cells are acraped into PBS containing 0.5 mM EDTA and 2 mM phenyl methylsulfonyl fluoride (PMSF). Drosophila cells are harvested from suspension cultures by centrifugation. Cells are washed twice in phosphate buffered saline and once in Buffer A (20 mM Tris-HCl pH 7.5, 150 mM EDTA, 1 mM PMSF, 0.25 TIU/ml aprotinin, 5 microMolar leupeptin, 25 mM benzamidine). The cells are then swollen in Buffer A without NaCl and lysed in a Dounce homogenizer. The lysates are cleared by low speed centrifugation. Membranes are pelleted twice at 100,000×g, resuspended in 50 mM hepes pH 7.0 ro 7.4, and stored at $-7°$ C. Membrane protein concentration is determined by the method of M. M. Bradford in Anal. Biochem. 72, 248-254 (1976).

Membrane protein is solubilized for NaDodSO$_4$P-AGE in 0.5% NaDodSO$_4$/10% glycerol/100 mM Tris.HCl, pH 6.8/0.03% bromophenol blue (mild conditions). For harsher denaturing conditions, 1% 2-mercaptoethanol is added to the solubilized membranes, and the samples boiled for 5 min before loading onto 6.5% polyacrylamide gels. NaDodSO$_4$/PAGE is performed as described by U. K. Laemmli in Nature (London) 227, 680-685 (1970).

Immunoblot hybridization is performed by the method of W. N. Burnette in Anal. Biochem. 112, 195-203 (1981) with the following modifications. The protein is transferred to nitrocellulose in a Transphor electrophoresis cell (Hoefer Scientific Instruments, San Francisco, Calif.) overnight at 4° C. (4 V/cm) in 15.6 mM Tris HCl, pH 8.3, 120 mM glycine, 20% (vol/vol) methanol. The filters are incubated in blocking medium (1% bovine hemoglobin in phosphate-buffered saline with 0.2% NaN$_3$) prior to probing with anti-EGF receptor antiserum (1:1000 dilution), or rabbit preimmune serum (1:50 dilution) for 3 hr at room temperature on a clinical rotator. The filters are washed once in blocking medium and twice in phosphate-buffered saline. Each filter is then incubated with 1 to 2×10$^6$ cpm of $^{125}$I-protein A in blocking medium for 2 to 3 hr. The filters are washed, dried, and subjected to autoradiography. The markers used for molecular weight determination are either prestained or stained after transfer with amido black.

Affinity Labeling of Immunoprecipitates: The dp100 protein is found in the membranes and cytoplasm of the Drosophila cells. Membrane protein is solubilized in 1 to 2% Triton X-100, 10% glycerol, 50 mM Hepes, pH 7.0, for 60 min at 4° C. Typically, 500 microgram of Drosophila membrane protein or 100 microgram of Swiss 3T3 membrane protein are used per sample. Unsolubilized material is removed by centrifugation at 12,000 x g for 10 min. The solublized membrane protein or cytoplasmic protein is diluted 1:2 and precleared by incubation with protein A-Sepharose beads (Pharmacia Fine Chemical Co., Piscataway, NJ). The cleared supernatants are treated overnight with anti-EGF receptor antiserum (1:10 dilution), anti-insulin receptor antiserum (1:50), or rabbit preimmune serum (1:10), and the product precipitated with protein A-Sepharose beads.

The immunopellets are washed three times with 50 mM Hepes, pH 7.0, 50 mM NaCl, 10% glycerol, 0.1% Triton X-100 and resuspended in 25 mM Hepes, 50 mM NaCl, 0.1% Triton X-100, 1 mg of bovine serum albumin per ml. 125I-EGF (35 nM) or 125I-insulin (20 nM) is added, and the samples incubated 60 min at 15° C. Binding specificity is tested by the simultaneous addition of a 1000-fold excess of unlabeled ligand (30 microM) and labeled ligand. Bound growth factor is crosslinked to the immunoprecipitates by addition of disuccinimidyl suberate to 0.4 mM and incubation for 15 min at 0° C. The samples are then centrifuged and the supernatant removed. The pellets are resuspended in sample buffer (33 mM Tris.HCl, pH 6.5, 2% NaDodS04, 10% glycerol, 0.1% bromophenol blue, 2% 2-mercaptoethanol) and boiled. The protein A-Sepharose beads are removed by centrifugation, and the supernatants run on 6.5% polyacrylamide/NaDodS04 gels.

In the competitive binding studies, the extent of 125I-insulin binding to the 100 kDa protein is quantitated by scanning that region of the gel with an LKB microdensitometer connected to an HP integrator. To ensure linearity, several exposures are taken. Dissociation constants are determined by statistical analysis.

Affinity Labeling of Membranes: Membrane from Schneider L2 and Swiss 3T3 cells in 50 mM Tris HCl (pH 7.2) or crude insulin receptor preparation from human placenta is incubated with 2 nM 125I-insulin for 60 min at 15° C. and crosslinked as described above for the immunoprecipitates. Excess unlabeled insulin (35 microM) is added to a duplicate sample to determine specific binding. The samples are boiled in solubilization buffer containing 3 mM dithiothreitol and subjected to electrophoresis on 7.5% polyacrylamide NaDodSO$_4$ gels.

Growth factor binding to A431 cells: A431 cells are grown in monolayer and 125I-labelled EGF bound to the cells as described by B. Friedman et al in *Proc. Natl. Acad. Sci. U.S.A.* 81, 3034–3039 (1984).

Two membrane proteins from Drosophila Schneider L2 cells are identified by immunoblot hybridization with polyclonal anti-EGF receptor antiserum. One, a protein of approximately 190 kDa, is the predominant high molecular weight species recognized by the anti-EGF receptor antiserum. This protein is the sole protein detected in the molecular weight range of the EGF receptor (170 kDa) when Drosophila membranes are solubilized in 0.5% NaDodSO$_4$ and applied to a NaDodSO$_4$/polyacrylamide gel without sample boiling or reduction. The 100 kDa protein that is capable of binding both EGF and insulin, dp100, is consistently observed under both immunoblotting conditions. Dp100 crossreacts with antisera against both EGF and the rat insulin receptor. These antigenically-related Drosophila proteins can act as receptors for EGF or insulin, as measured by their ability to bind the mammalian growth factor by affinity labeling. Affinity labeling of 125I-insulin to dp100 can be detected after incubation of the ligand with intact membranes. Specific binding of 125I-EGF to intact Drosophila membranes is not detected by affinity-labeling experiments.

To increase sensitivity of detection, detergent-solubilized membranes from Drosophila-cultured cell lines are immunoprecipitated with anti-EGF receptor antiserum, anti-insulin receptor antiserum, or rabbit preimmune serum prior to affinity labeling. Radiolabeled growth factors are added to the immune precipitates in the presence or absence of excess growth factor, allowed to bind at 15° C., and then crosslinked with disuccinimidyl suberate. Samples are analyzed by separation on NaDodSO$_4$/PAGE and subsequent autoradiography. Anti-insulin receptor antiserum does not immunoprecipitate any Drosophila proteins to which binding of 125I-insulin can be detected, although it recognizes bands of 100 kDa (dp100) and 120 kDa in immunoblot hybridizations. However, the anti-EGF receptor antiserum does specifically immunoprecipitate dp100. Similar results are observed when membrane proteins from two different Drosophila cell lines, Schneider L2 and K$_c$, are analyzed. An excess of either unlabeled EGF or insulin can block binding of both 125I-insulin and 125I-EGF to the dp100, demonstrating that this protein has a common binding site for both growth factors.

The dp100 has a higher affinity for insulin than EGF. First, in crosslinking experiments with membranes, binding of 125I-insulin but not 125I-EGF is detected. Second, in competition experiments with unlabeled ligand, insulin is more effective than EGF at inhibiting both 125I-insulin and 125-EGF binding. The dual ligand specificity of the dp100 for EGF and insulin is surprising because mammalian EGF and insulin receptors do not share this property. For example, 125I-EGF, but not 125I-insulin, can be crosslinked to the 170 kDa EGF receptor immunoprecipitated from murine 3T3 fibroblast membranes by anti-EGF receptor antiserum. Similarly, the affinity labeling of the murine EGF receptor by 125I-EGF can be blocked by excess EGF but not by excess insulin.

Affinity labelling experiments with the 125I-labelled ligands demonstrates that the binding specificity of dp100 extends to other growth factors structurally similar to insulin and EGF. Dp100 can be affinity labelled with all the insulin-like and EGF-like growth factors tested: TGF-alpha, EGF, insulin, and IGF-I. Further, radiolabelled growth factor binding can be inhibited in all cases by addition of excess unlabelled insulin or the specific ligand. However, neither 125I-TGF-beta nor 125I-PDGF, two structurally unrelated growth factors, can be crosslinked to dp100 or any other immunoprecipitated Drosophila protein under these conditions. Controls with preimmune serum fail to immunoprecipitate dp100 or any other growth factor binding protein.

The relative binding affinities of these and other hormones were determined by competitive affinity labelling experiments using 125I-insulin as a label. The competetive binding curves for TGF-alpha, insulin and EGF (FIGS. 1a and 11b), derived from densitometric scanning of the autoradiograms, were used to calculate the relative binding affinities in Table 1. The dissociation constants ranged from $10^{-6}$ M to $10^{-9}$ M.

The measured dissociation constants fall within the mammalian physiological range. In contrast, hormones and growth factors that are not members of these families do not bind or bind with dissociation constants that are greater than $10^{-6}$ M. Further, the insulin and EGF-like factors compete with one another for binding to dp100. These results indicate that the insulin-like and EGF-like growth factors can compete for binding with high specificity to a single protein.

TABLE 1

| Dissociation constants for ligand binding to dp100 | |
|---|---|
| LIGAND | K$_D$(n)a |
| TGF-alpha | $5 \times 10^{-9}$ |
| EGF | $1.3 \times 10^{-6}$ |

TABLE 1-continued

Dissociation constants for ligand binding to dp100

| LIGAND | $K_D(n)a$ |
| --- | --- |
| INSULIN | $1.1 \times 10^{-7}$ |
| IGF-I | $5 \times 10^{-7}$ |
| IGF-II | $1.3 \times 10^{-8}$ |

Synthetic human transforming growth factor-alpha (TGF-alpha) and insulin-like growth factor-II (IGF-II) bind with the highest affinities, Kd of $5 \times 10^{-9}$ M and $1.3 \times 10^{-8}$ M, respectively. EGF, insulin and insulin-like growth factor-I (IGF-I) bind with dissociation constants ranging from $10^{-6}$ M to $10^{-7}$ M. Nerve growth factor (NGF), glucagon and pituitary thyroid hormone (PTH) show some ability to compete but the dissociation constants are higher than $10^{-6}$ M. The amino terminal fragment of urokinase (ATF), which binds to the urokinase receptor with an affinity comparable to that of the native enzyme, does not compete with $^{125}$I-insulin at concentrations up to $3 \times 10^{-6}$ M. It should be noted that all the ligands tested were from mammalian sources and thus are not the endogenous ligands for dp100. The affinity of dp100 for TGF-alpha and IGF-II is at least as high as that reported for the binding of porcine insulin to the Drosophila insulin receptor. These results indicate that dp100 binds to mammalian insulin-like and EGF-like growth factors with a high affinity and specificity for a heterologous system.

Dp100 binds to synthetic human TGF-alpha with an affinity three orders of magnitude higher than that for EGF and has the unique ability to bind and differentiate between these two ligands. To ensure that the difference in the binding affinities of EGF and TGF-alpha for dp100 reflects a property of the protein rather than the particular growth factor preparations, the ability of unlabelled EGF and TGF-alpha to compete with $^{125}$I-labelled EGF for binding to the EGF receptor in human epithelial carcinoma A431 cells was determined.

Figure 2:
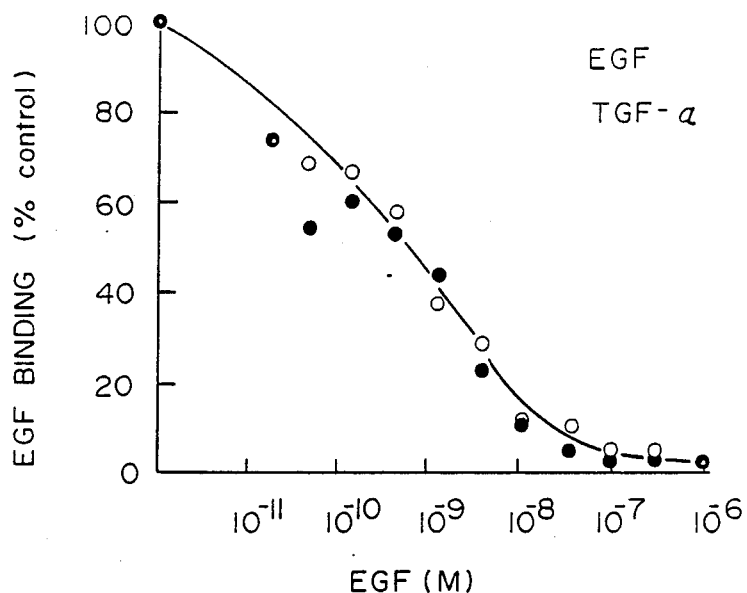
FIG. 2 is a graph of the competitive binding of murine EGF and synthetic human TGF-alpha to the EGF receptor in A431 cells. $^{125}$I-EGF ($10^5$ cpm) was incubated with A431 cells ($2 \times 10^4$ cells/well) at 4° C. for 3 hr in the presence of different M concentrations of unlabelled EGF (●) or TGF-alpha (○). The percent of binding as compared to the control is the mean of duplicate determinations with the error less than 10%.

As shown in FIG. 2, there is no significant difference in the affinities of the EGF and TGF-alpha preparations for the mammalian EGF receptor. The data presented here implies that dp100 recognizes EGF and TGF-alpha in a different way than the EGF receptor. The fact that dp100 and the mammalian EGF receptor are both able to recognize EGF and TGF-alpha suggests that there is a common recognition site in their binding domains. However, some specific recognition sites of dp100 and the EGF receptor must differ because only dp100 can differentiate between the two growth factors.

Figure 3:
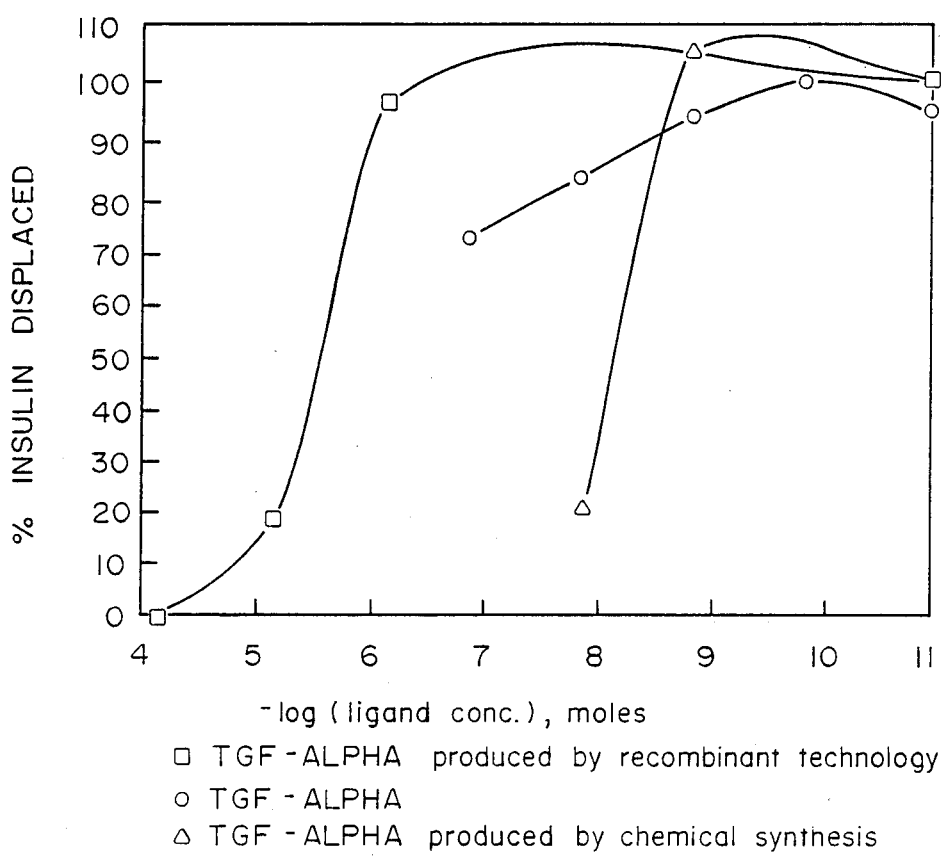
FIG. 3 is a graph comparing the binding affinity of dp100 to native TGF-alpha (○), TGF-alpha that has been synthesized chemically (△), and TGF-alpha that has been produced in E. coli using recombinant DNA technology (◻).

Furthermore, dp100 is able to differentiate on the basis of binding affinity between native TGF-alpha, TGF-alpha that has been synthesized chemically, and TGF-alpha that has been produced in E. coli using recombinant DNA technology (Genentech, San Francisco, Calif.). Human synthetic TGF-alpha binds to dp100 with an affinity that is 100-1000 times greater than that of human recombinant TGF-alpha. Native EGF and native TGF-alpha bind with affinities within the same order of magnitude as the recombinant form. Since the sequences are identical, the differences in binding affinity presumably arise from differences in conformation of the growth factor preparations. This is not surprising, since both the synthetic and recombinant forms are oxidized to form the appropriate disulfide bridges. These results, shown in FIG. 3, establish that this protein can be used as a diagnostic tool to distinguish between conformational states of TGF-alpha and related peptides. Since the native TGF-alpha is difficult to isolate and recombinant or synthetic peptides are the major species presently available (as well as economically feasible for companies to produce), dp100 is a potentially valuable tool to assess the relationship of newly synthesized proteins to the native forms of EGF and TGF-alpha. This concept can be expanded to include any native binding proteins that normally discriminate between different ligands on the basis of binding affinity.

The binding of the dp100 protein allows it to be used in direct screening assays for EGF and EGF-like molecules. One use of such an assay wherein the binding affinity of the protein is measured is in determining whether or not a genetically engineered and produced EGF or TGF-alpha molecule has properly assumed the three dimensional structure required for in vivo functionality. An advantage to the present protein over the EGF receptor is its broader specificity, allowing measurement of proteins not having the exact same structure as the EGF molecule.

Many of these molecules, including EGF and TGF-alpha, are secreted by embryonic and cancerous cells. An assay which can detect the production of EGF or an alteration in the binding affinity of EGF produced by specific cells may therefore be used as an indicator that transformation of the cells has occurred.

Another use for the dp100 protein is in drug design. For example, study of the binding site for the dp100 protein provides a means for designing a drug which has similar binding properties. It also serves as a means for assaying for the effectiveness of a compound in blocking the binding of proteins such as EGF or TGF-alpha. These compounds are potentially useful as inhibitors of proliferation of tumor cells. The dp100 protein has the advantage in such assays over proteins such as antibodies because of their wide specificity, with respect to the number of proteins to which it will bind, and high specificity for the binding site, which provides a maximum of flexibility in design of assays based on binding affinities.

Dp100 can also be used to purify or remove EGF, TGF or related proteins from a solution or from the blood of a patient with tumor cells producing high levels of these substances.

This invention has been described with reference to specific embodiments of the dp100 protein and assays utilizing the protein. Modifications and variations of the protein and assays will be obvious to those skilled in the art from the detailed description of the invention. Such modifications and variations are intended to come within the scope of the appended claims.

We claim:

1. A protein comprising
   a 100 kDa cellular protein isolated from Drosophila cells, wherein said protein binds mammalian epidermal growth factor, transforming growth factor-alpha and insulin and is recognized by antisera directed against the mammalian epidermal growth factor receptor.

2. The protein of claim 1 isolated from Drosophila Kc cells.

3. The protein of claim 1 isolated by harvesting Drosophila cells from a culture, lysing the harvested Drosophila cells, isolating the proteins from the lysed cells, and binding said Drosophila protein to an epidermal growth factor-like or insulin-like protein.

4. The protein of claim 3 further comprising separating the cell membranes and solubilizing the membrane proteins.

5. The protein of claim 3 wherein said protein binds with a second protein selected from the group consisting of anti-EGF receptor antibodies, anti-insulin receptor antibodies, EGF, and insulin.

6. The portein of claim 5 wherein the second protein is bound to Protein A-Sepharose.

* * * * *

UNITED STATES PATENT AND TRADEMARK OFFICE
CERTIFICATE OF CORRECTION

PATENT NO. : 4,774,321

DATED : September 27, 1988

INVENTOR(S) : Marsha R. Rosner et al.

It is certified that error appears in the above-identified patent and that said Letters Patent is hereby corrected as shown below:

Abstract, line 10, delete "$10^{-6}M$ to $10^{-9}M$" and insert --$10^{-6}M$ to $10^{-9}M$--.

Column 3, line 35, delete "ar" and insert --are--.

Column 3, line 49, insert --,-- after "Jacobs".

Column 3, line 55, delete "H. Massague" and insert --J. Massague--.

Column 4, line 9, delete "acraped" and insert --scraped--.

Column 4, line 15, before "EDTA" insert --NaCl, 1mM-- and after "EDTA," insert --1mM EGTA--.

Column 4, line 20, delete "hepes" and insert --Hepes-- and delete "ro" and insert --or--.

Column 4, line 21, delete "-7°C" and insert -- -70°C--.

Column 4, lines 24 and 25, delete "NaDodSO$_4$PAGE" and insert --NaDodSO$_4$/PAGE--.

Column 5, line 5, delete "125I-EGF (35nM) or 125I-insulin" and insert --$^{125}$I-EGF (35nM) or $^{125}$I-insulin--.

Column 5, line 19, delete "125I-" and insert --$^{125}$I--.

Column 6, line 51, delete "11b" and insert --1b--.

UNITED STATES PATENT AND TRADEMARK OFFICE
CERTIFICATE OF CORRECTION

PATENT NO. : 4,774,321

DATED : September 27, 1988  Page 2 of 2

INVENTOR(S) : Marsha R. Rosner et al

It is certified that error appears in the above-identified patent and that said Letters Patent is hereby corrected as shown below:

Column 6, line 51, delete "11b" and insert --1b--.

Signed and Sealed this

Seventh Day of November, 1989

*Attest:*

JEFFREY M. SAMUELS

*Attesting Officer*   *Acting Commissioner of Patents and Trademarks*